United States Patent [19]

Corby, Jr.

[11] Patent Number: 5,253,169

[45] Date of Patent: Oct. 12, 1993

[54] METHOD AND APPARATUS FOR REDUCING X-RAY DOSAGE DURING FLUOROSCOPIC EXAMINATIONS

[75] Inventor: Nelson R. Corby, Jr., Scotia, N.Y.

[73] Assignee: General Electric Company, Schenectady, N.Y.

[21] Appl. No.: 800,379

[22] Filed: Nov. 29, 1991

[51] Int. Cl.$^5$ .............................................. G06F 15/00
[52] U.S. Cl. .................................. 364/413.13; 382/6; 382/56; 128/654
[58] Field of Search ................ 364/413.13; 382/6, 21, 382/27, 55, 56; 128/654, 656

[56] References Cited

U.S. PATENT DOCUMENTS

| | | | |
|---|---|---|---|
| 4,459,990 | 7/1984 | Barnea | 128/656 |
| 4,680,709 | 7/1987 | Srinivasan et al. | 382/6 |
| 4,922,332 | 5/1990 | Taniguchi et al. | 358/77 |
| 4,998,972 | 3/1991 | Chin et al. | 128/6 |
| 5,036,464 | 7/1991 | Gillien et al. | 364/413.13 |
| 5,119,445 | 6/1992 | Suzuki et al. | 382/55 |

OTHER PUBLICATIONS

Thesis–Three Dimensional Navigation Assist for Interventional Radiological Procedures, submitted to the Graduate Facility of Rensselaer Polytechnic Institute on Dec. 1990, Jonathan A. Zarge.

Primary Examiner—Roy N. Envall, Jr.
Assistant Examiner—Frantzy Poinvil
Attorney, Agent, or Firm—Paul R. Webb, II

[57] ABSTRACT

An apparatus for reducing accumulated X-ray dosage during a fluoroscopic examination adaptively varies the time between exposures, X-ray beam strength, and beam extent and aim point during the course of the procedure in real-time. A temporal sequence image analyzer identifies a catheter in the fluoroscopic image and forms a prediction of its movement based on a time-series of fluoroscopic images. This prediction model is used to modulate the X-ray beam to produce a much smaller fluoroscopic image including only the area in the vicinity of the catheter tip. An output image synthesizer produces a useful output image by combining these stored sub-images.

16 Claims, 12 Drawing Sheets

```
CHAIN 1: 1   2   3   4   5   6   7   8   9   10  11  12  13  22
CHAIN 2: 22  14  15  16  17  18
CHAIN 3: 22  19  20  21
CHAIN 4: 22  23  24  25
CHAIN 5: 25  26  27  28
CHAIN 6: 25  29  39  31  32  33  34
CHAIN 7: 35  36  37  38
CHAIN 8: 39  40  41  42  43  44  45  46  47  48  49  50  51  52  53  54
``` fig. 13
```
V         9 10 16
V         9 10 11 12
V         9 10 11 13 14
V         9 10 11 13 15 17
V         9 10 11 13 18
V    2 4 5 8 10 16
V    2 4 5 8 10 11 12
V    2 4 5 8 10 11 13 14
V    2 4 5 8 10 11 13 15 17
V    2 4 5 8 10 11 13 18
V    1 4 5 8 10 16
•••  (18 PATHS OMITTED)  •••
V    7 5 8 10 16

V         3 1 2 6 5
I         3 1 2 6 4 3
I         3 1 2 6 4 1
V         3 1 2 7 8 9 10 12
V         3 1 2 7 8 9 10 11
V         3 1 2 7 8 11 12
V         3 1 2 7 8 10 9
V         3 1 2 7 9 8 10 12
V         3 1 2 7 9 8 10 11
V         3 1 2 7 9 11 12
V         3 1 2 7 9 1 10 9
V         3 1 2 7 10 12
V         3 1 2 7 10 11 8
V         3 1 2 7 10 11 9
I       5 4 1 2 6 5
I       5 4 1 2 6 4 3
I       5 4 1 2 6 4 1
V       5 4 1 2 6 8 9 10 12
•••  (163 PATHS OMITTED)  •••
I  9 11 10 7 6 4 1 2 7 10 11 9
```

METHOD AND APPARATUS FOR REDUCING X-RAY DOSAGE DURING FLUOROSCOPIC EXAMINATIONS

This invention relates generally to fluoroscopy procedures and more specifically to a method for reducing the X-ray dosage required during such procedures, while still providing a physician with an image stream equivalent to that produced by a standard fluoroscope system.

RELATED APPLICATIONS

The present application is related to commonly assigned and copending U.S. patent application Ser. Nos. 07/800,377 and 07/800,374 both filed Nov. 29, 1991, entitled respectively, Method and Apparatus for Real-Time Tracking of Catheter Guide Wires in Fluoroscopic Images During Interventional Radiological Procedures and Method and Apparatus for Real-Time Navigation Assist in Interventional Radiological Procedures.

BACKGROUND OF THE INVENTION

Interventional Radiological (IR) procedures are gaining importance as cost effective methods to effect therapeutic actions within the body. In these procedures a physician attempts to guide a catheter along the vascular network to a remote internal site within the patient using real-time fluoroscopic imagery for visual feedback. A fluoroscope system consists of an X-ray source positioned below a patient lying on a table and a two-dimensional detection screen coupled to a two-dimensional image intensifier positioned above the patient. A standard fluoroscope produces an equispaced temporal sequence of radiographic images of whatever lies between the X-ray source and the detection screen. A manually adjusted set of shutters at the X-ray source (positioned at the start of the procedure) determines the direction and spatial extent of the beam. The X-ray beam intensity is adjustable either manually or in some commercial systems, semi-automatically, to give proper image exposure. The patient/physician dosage is determined jointly by the beam intensity, the area of the beam, and the number of frames taken.

The trend is to attempt increasingly complicated procedures that require traversing the vascular system to increasingly remote sites within the body. The fluoroscope is the primary tool that the physician uses to enable him to thread a catheter to a remote internal site. It allows him to visualize the internal vasculature and to gauge the position and orientation of the catheter relative to the vasculature. As the destination site becomes more remote, the time to get there increases rapidly. The fluoroscope typically is energized for a sizable percentage of the total procedure time, resulting in significant accumulated patient X-ray dosage. For the patient this will probably be an isolated dose. However, the physician, because he performs many procedures per year, can accumulate a dangerous dosage level. The physicians can adjust the system operating parameters to limit the dosage to the absolute minimum while maintaining sufficient image quality to allow manipulation, but in many cases existing systems do not provide entirely risk-free use.

Existing systems expose a large area of the patient to the X-ray beam to provide the physician with a full field of view on each exposure. Typical systems acquire images every 33 milliseconds resulting in an extremely large accumulated dosage of X-rays for patient and doctor.

Some existing systems adjust the beam current of the X-ray tube on a frame by frame basis based on measuring overall image brightness of the most current image. Typically, the mean value of the brightness histogram is used to raise or lower beam strength. The analysis is entirely global and does not depend on recognizing and tracking local scene activity or content. Thus, what is required is a fluoroscope system that automatically and continuously adjusts the system parameters (X-ray beam shape, application point, beam intensity, and the time interval between exposures) by real-time analysis of the images produced by the system in such a way as to preserve maximum fidelity of manipulation information while reducing the X-ray dosage to a minimum.

SUMMARY OF THE INVENTION

In accordance with the present invention, there is provided a method and apparatus for reducing X-ray dosage during fluoroscopic examinations by adaptively varying one or more system parameters (time between exposures, beam strength, beam extent and aim point) during the course of the procedure (in "real-time") based on the identification of a target object (i.e., the catheter guide wire) and changes in the targets appearance. An estimate of the motion of the catheter is formed and, based on the estimate, the X-ray beam is modulated so that the image of the catheter tip is within the image produced by the modulated X-ray beam at the time the next exposure occurs. The method, in essence, significantly reduces the spatial extent of the X-ray beam, in real-time, by predicting the motion of the catheter and exposing only an area corresponding to the estimated location and shape of the tips of the catheter at the time the next frame is to be taken.

By periodically switching to full field of view mode, the method is able to maintain an output image which is created by fusing the latest full field of view image with each of the sub-images. The output image provides the physician with real-time imagery, over the full field of view, to allow him to asses the progress of catheter placement. The information provided by the full field of view image varies "slowly" (perhaps 1-5 frames/second) and serves only to set the general anatomical framework and therefore needs to be updated less often than the catheter tip itself. The present invention can additionally increase the temporal spacing of images when catheter motion is relatively predictable, thus decreasing the X-ray dosage by taking fewer images.

DESCRIPTION OF THE DRAWINGS

FIG. 13 illustrates paths derived from a simple test image and a complex test image.

DESCRIPTION OF THE INVENTION

The present invention is directed to an apparatus and method for reducing the X-ray dosage during fluoroscopic examinations. X-ray dosage is reduced in three ways: by reducing the spatial extent of the X-ray beam, by reducing the intensity of the X-ray beam, and by reducing the number of exposures taken during a procedure. These benefits are realized without compromising on the quality of the output image which the physician uses as visual feedback while advancing the catheter to its intended destination.

Figure 1:
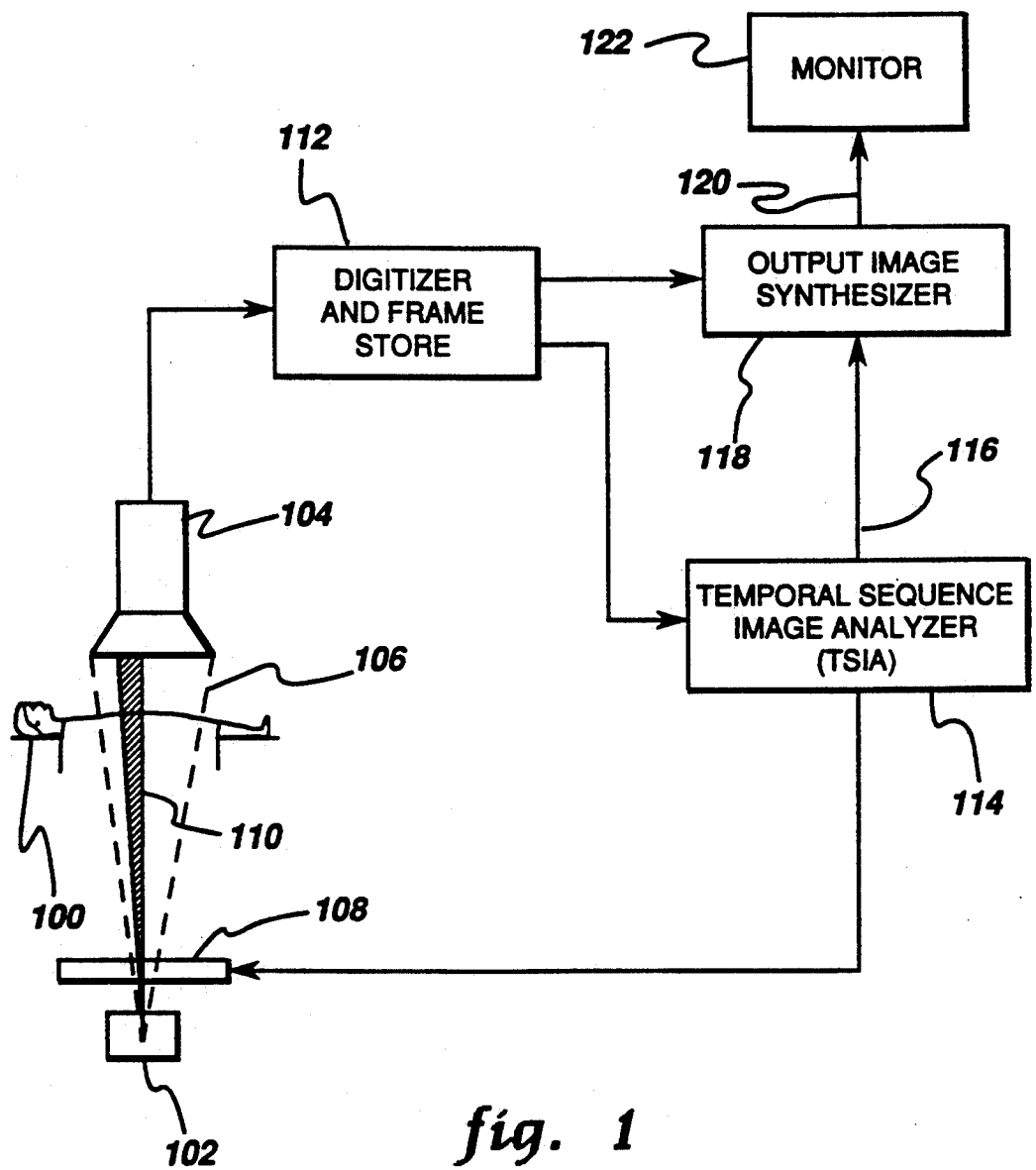
FIG. 1 is an overview of the method and apparatus for reducing X-ray dosage, showing the three major functional elements of spatial beam modulation, temporal sequence image analysis, and output image synthesis.

As shown in FIG. 1, the apparatus of the present invention has three major parts: a time variable spatial X-ray beam modulator for adjusting the spatial extent of an X-ray beam in space 108, a temporal sequence image analyzer 114 (TSIA) for locating the image of a catheter in a series of fluoroscopic images, and an output image synthesizer 118 for creating a composite image from a series of sub-images. This figure shows how these three major parts function to achieve the reduction in X-ray dosage. A patient 100 is shown positioned in a fluoroscope which consists of an X-ray source 102 and a detection screen 104. The patient is undergoing an interventional radiological procedure whereby a catheter is inserted into the patient's vascular system through a puncture in the skin. The catheter consists of a guide wire surrounded by a sleeve portion wherein the guide wire can be retracted or advanced during the procedure. Once the sleeve has reached a desired location in the patient's body, the catheter guide wire may be removed and reinserted to the same site easily by simply pushing the guide wire through the sleeve.

In conventional fluoroscopic practice, the X-ray source 102 produces a nominal beam shape 106 which provides maximum exposure to the patient and utilizes the full detection screen area 104. In this fluoroscope, the signal generated from the detection screen 104 is sent to a video monitor (not shown in FIG. 1) for display. Some fluoroscopes have more advanced features such as the ability to digitize the video output and to store selected "frames" when selected by a physician viewing the display.

Modulator 108 of the present invention is positioned between the patient and the X-ray source. The function of the modulator 108 is to create an X-ray transparent aperture in the middle of X-ray opaque screen 104. The aperture will spatially limit the raw X-ray beam 106 or an adaptive beam shape 110, thereby creating a two-dimensional X-ray beam with the desired extent, shape, and direction (relative to the X-ray point source of the X-ray generator) necessary to cause an image of the catheter tip to appear on the detection screen 104. The aperture has to be capable of rapidly (10-30 milliseconds) assuming the desired shape.

Figure 2A:
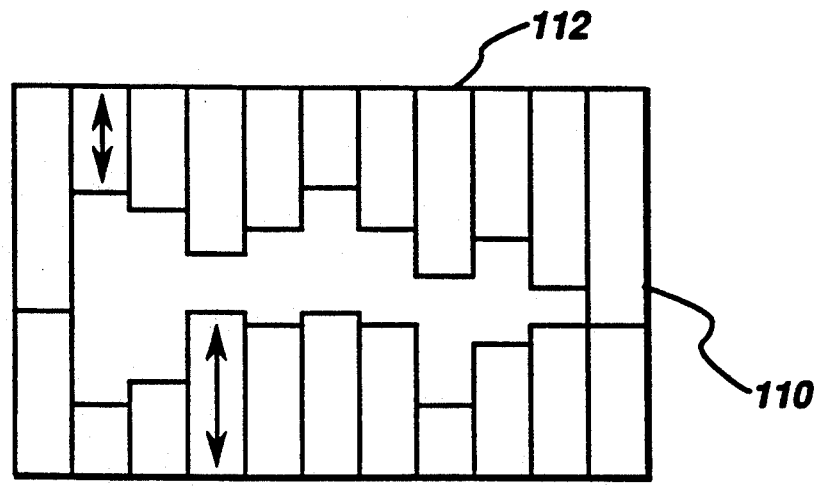
FIGS. 2a and 2b show an embodiment of a spatial beam modulator.
Figure 2B:
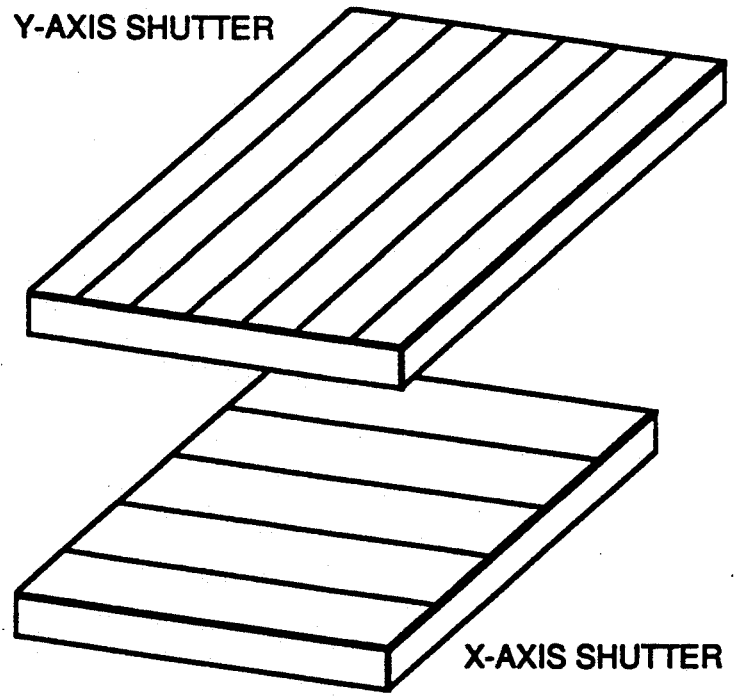

FIG. 2a shows a preferred embodiment of modulator 108. Two rows of narrow vertical strips 112 of X-ray attenuating material such as aluminum or lead are arranged as shown. For each vertical pair of strips, there are two drive motors, one for the lower and one for the upper strip. Each motor can independently extend or retract its strip, thus forming a narrow rectangle of variable height at a variable location. By using a large number of strips, any shape may be approximated, provided it is not concave from side to side. In order to allow for any general concave or convex shape, a second strip shutter is placed at right angles to to the first strip shutter assembly as shown in FIG. 2b. If it is desired to have a gradual transition in X-ray attenuation around the aperture (rather than an abrupt 0–100% transition), a number of strips could be stacked vertically in each strip shutter assembly. Each of the stacked strips would be actuated independently. The stacked strips would form a stairstep approximation to the 0–100% profile.

An alternate method with less flexibility would be a moveable, circular aperture formed of crescent shaped leaves much like those found in the iris diaphram of a film camera. The aperture could be moved to any x-y position. While the arbitrarily shaped aperture would provide a more exact match to the desired shape, the circular (or possibly elliptical) aperture would suffice in many cases. The advantage of a variable size, fixed shape aperture would be in the ease of fabrication, simplicity of design and simplicity of control.

Referring again to FIG. 1, each frame of video output from detection screen 104 is fed to a digitizer and frame store 112 where the video frame is digitized into an image consisting of discrete pixels (picture elements) which are assigned a value on a scale from white to black. The digitized images are in turn fed to the TSIA 114 which is a computer that is programmed to locate the pixels, in a given image, corresponding to the catheter within patient 100. By reference to a current image and a number of previous images, the TSIA predicts the location and orientation of the image of the catheter at the time the next frame is to be taken. The TSIA uses this information, together with the angular orientation of the X-ray source relative to the patient being imaged, to determine the shape and position of the aperture in modulator 108.

Spatial filter functions 116 are computed by the TSIA and sent to the output image analyzer 118. These filter functions define for each pixel in the current image, the weight to be given to that pixel in the output image 120, which is a composite of n previous images. At least one of the images must be one generated with a nominal beam shape 106 so that the background anatomical information is provided in the output image 120. The output image synthesizer 118 combines n successive images using the filter functions computed by the TSIA. The filter functions can consist of ones for pixels corresponding to the catheter image and zeros for all other pixels. The filter functions can be used for contrast adjustment in the output image 120. The primary function is to form a real-time sequence suitable for manipulation. The output image 120 is sent to video monitor 122 for display.

The TSIA utilizes an algorithm consisting of two parts, peak finding (see FIG. 3) and two-dimensional model building (see FIG. 4) to identify the set of two-dimensional pixels which define the catheter image. The goal of the peak finding module is to determine which pixels (two-dimensional picture elements) in the images correspond to the catheter guide wire. Next, these pixels are scanned for connectivity to other guide wire pixels which eventually results in a two-dimensional model (linked list of pixels) of the catheter guide wire in the image plane.

Figure 3:
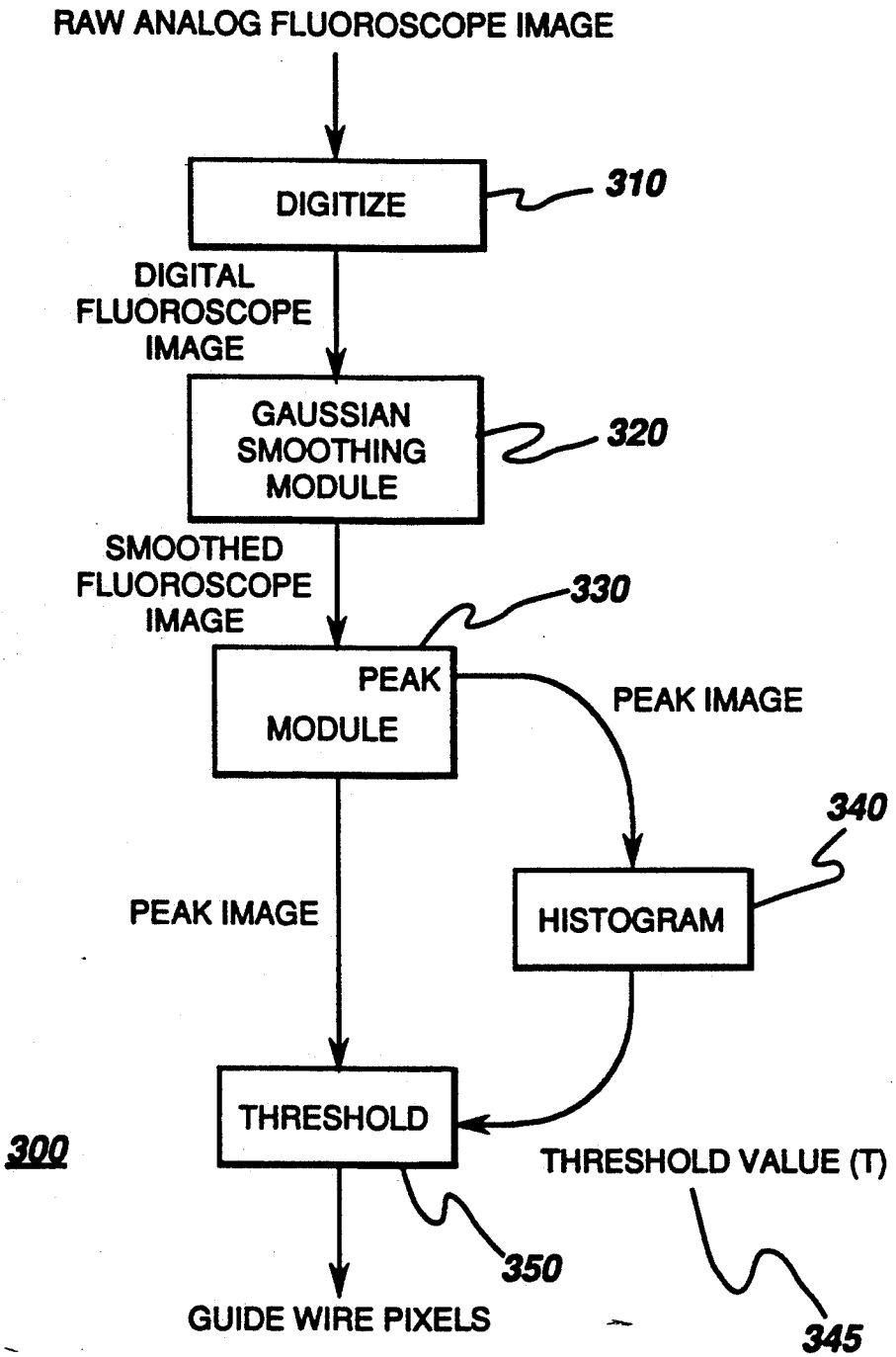
FIG. 3 is a flowchart diagram for the peak finding module.

FIG. 3 shows one possible algorithm used to locate the catheter guide wire pixels. First the image is digitized at block 310. Next, the image is smoothed with a 5×5 Guassian kernal at block 320. Second derivative values for each pixel are computed in the four principle directions; horizontal, vertical, and the two diagonals. Rotated variations of [1-2 1] are used. The [1-2 1] kernals implement the second derivative operation. The peak module 330 converts a raw image into a peak image. For every pixel P in the image, the maximum of the four second derivatives is computed by convolving the image with the kernals described above and taking the maximum of those four values. Next, each pixel is tested to determine if it is a maximal gradient point in the direction from which the maximal value was discovered. If it is, the value of pixel P is set to that maximal value, if not, P is set to a low value (lower than any of the maximal gradient values). The resulting image is a peak image of the original raw fluoroscopic image.

Figure 4:
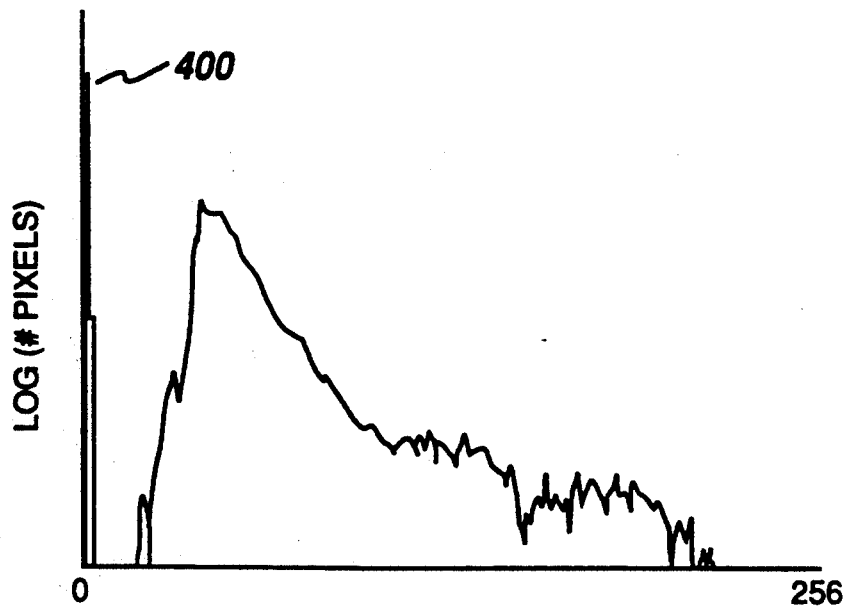
FIG. 4 is a peak image histogram for the sample image.
Figure 5:
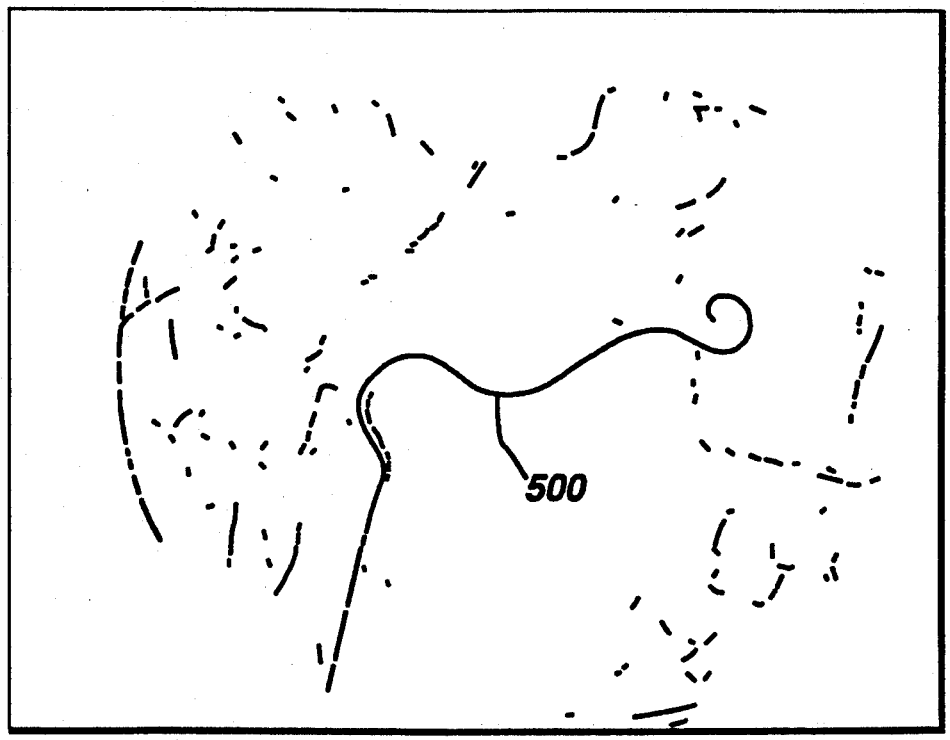
FIG. 5 is the output of the peak filter algorithm on the sample image.

The next step 350 is to find the proper threshold value for the peak image. For this, a histogram 340 is necessary. FIG. 4 shows a sample histogram. The histogram reveals that there is a large spike 400 of pixels whose value is at the low end of the range. Besides this spike at the minimum value, a more "normal" distribution of values exists over the remaining values in the peak image. Before the threshold value is computed, the image is masked to blank out all pixels near the edge of the image and outside of the circular region that defines the boundary of the fluoroscope data. Then, the proper threshold, T (345 in FIG. 3), is computed based on the histogram of the peak image data. In a preferred implementation, T is set to the mean plus two standard deviations (the mean and standard deviation for the peak image are computed based on peak image pixel values except those pixels whose value is at the minimum spike). FIG. 5 shows the resulting binary image. There are small breaks in the guide wire pixel chains but this problem will be discussed and solved hereinbelow. The binary peak image 500 is the input for the two-dimensional model creation module.

Figure 6:
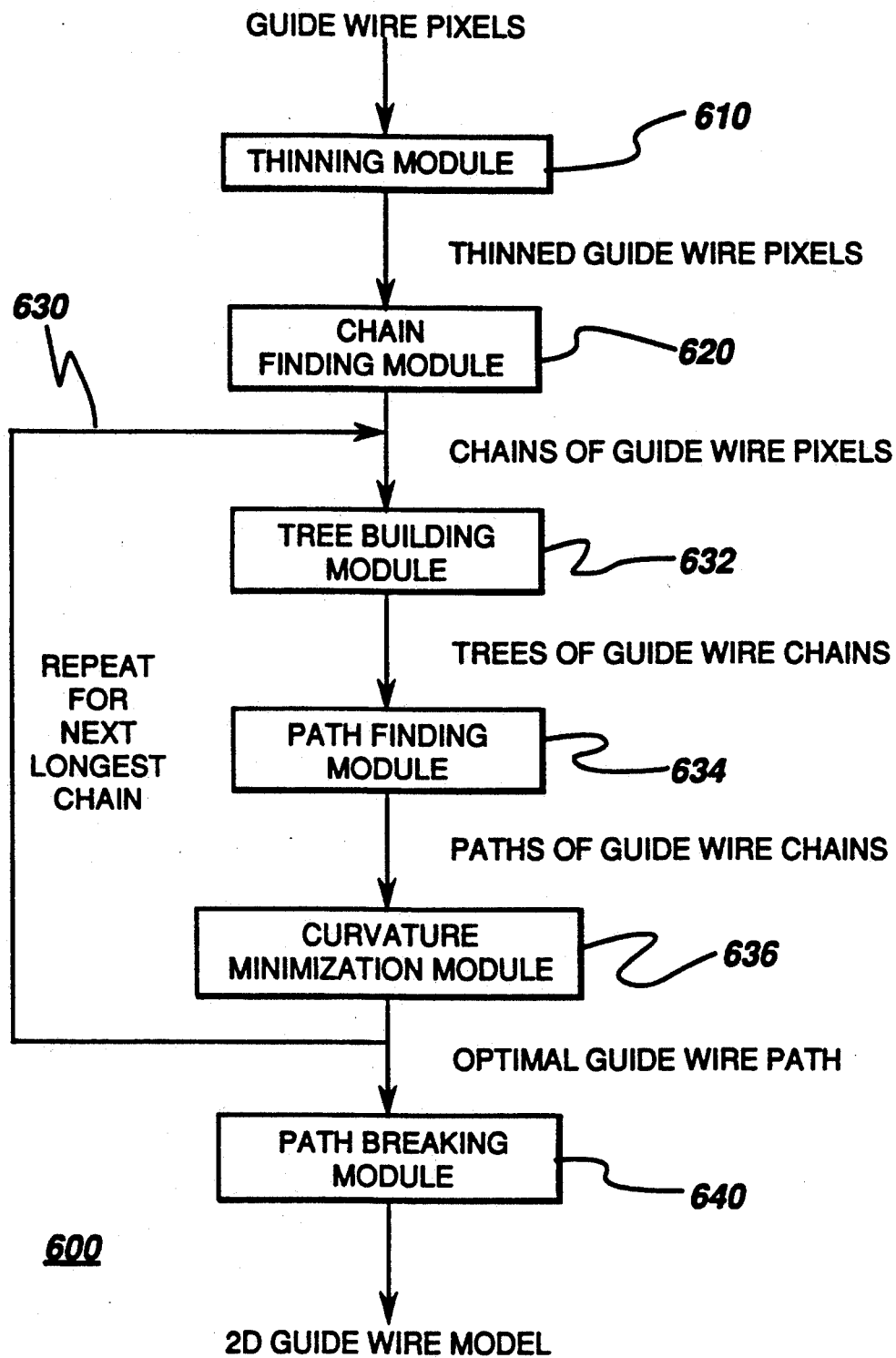
FIG. 6 is a flowchart diagram for the two-dimensional model creation sub-module.

FIG. 6 shows a two-dimensional model creation module 600. The goal of the two-dimensional model creation module 600 is to construct a two dimensional model of the catheter guide wire in the image plane. This is accomplished by several smaller modules shown in FIG. 6. The image is first thinned at block 610 so that all the lines in the image are only one pixel wide. Then, chains of pixels are identified at 620. Next, a set of longest connected paths is compiled from which the path with the least amount of curvature is selected (loop 630). Finally, this optimal path is broken into segments at 640 (based on local curvature) yielding a set of ordered vertices which can be saved as the two-dimensional catheter guide wire model in the image plane. Each of these modules will be described in detail in the following sections.

The first step 610 in two-dimensional model creation is thinning the peak image pixels in such a way that the genus of the image remains unchanged. The genus of an image is defined as the number of separated regions in an image. The neighbors of each pixel are scanned to determine if removing the pixel (setting it to the background color) will change the genus of the image. If removing the pixel will change the genus or if the pixel is an endpoint of a chain of pixels, then the pixel remains unchanged; otherwise, it is removed. This thinning process repeats until no pixels may be removed from the image.

Figure 7:
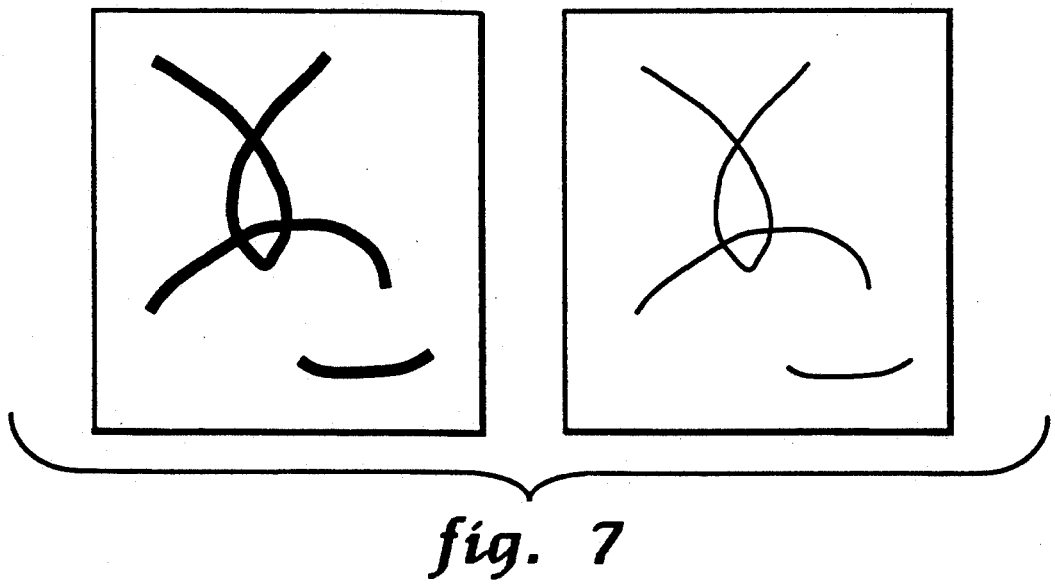
FIG. 7 illustrates thinning of a test image.

FIG. 7 shows two enlargements of a test image; one before thinning (on the left) and one after thinning (on the right). The square blocks in the thinned image on the right represent one pixel. Thinning the peak image is necessary for the chain finding module to function properly.

Referring again to FIG. 6, the pixels in the thinned peak image must be ordered into chains of pixels at block 620. This algorithm first examines the eight neighbors of each "on" pixel (not the background color) and counts the number of "on" neighbors of that pixel. If a pixel has two neighbors it is designated as a normal pixel; otherwise the pixel is designated as a juncture pixel. Therefore, ends of chains and intersection points become juncture pixels.

Figure 8:
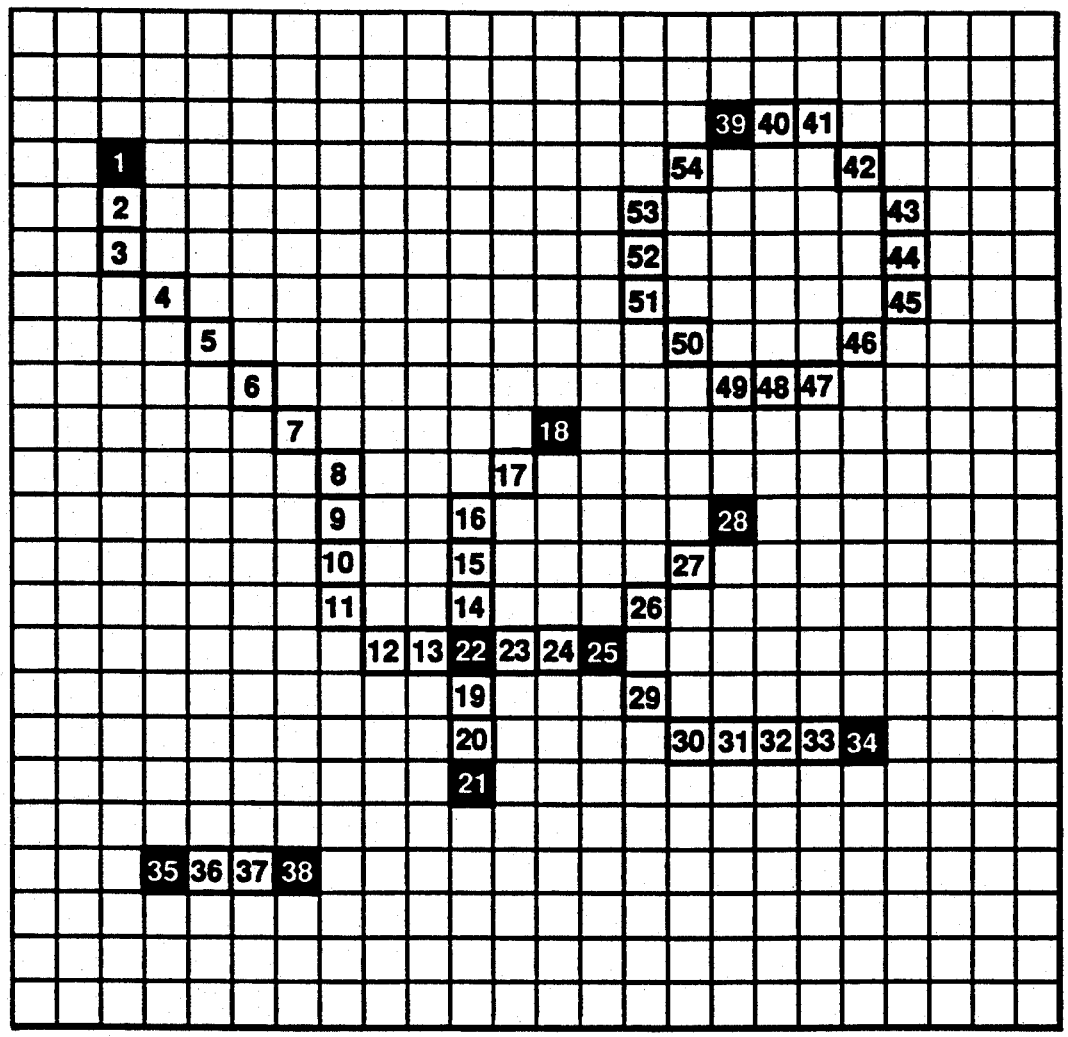
FIG. 8 illustrates chains of pixels in a test image.

FIG. 8 shows a small portion of a binary peak image; each box represents a pixel and the number inside of each box indicates its identification number. Normal pixels have black numbers in white boxes, juncture pixels have white numbers in black boxes, and background pixels have no numbers. In the chain finding module 820, chains are formed by traveling from one pixel to another starting at a juncture and ending at a juncture. The starting juncture pixel is designated the head of the chain and the ending juncture pixel is designated the tail of the chain. After all juncture pixel neighbors are processed, any remaining pixels are designated as being members of cycles; these chains of pixels do not contain any junctures. These pixels are processed in a special way. Within each cycle a random pixel is chosen to become a juncture pixel. At this point these cycles can be treated as the non-cyclic chains and traversed in the same way, from juncture to juncture (the starting and ending junctures are the same juncture; thus, the head and the tail of the chain are identical). The circle of pixels in the upper right hand corner of FIG. 8 exemplify a cycle. Using this algorithm, eight chains would be found in the image in FIG. 8; the chains are listed under the grid.

Referring again to FIG. 6, steps 632-636 find a group of chains which form the optimal path corresponding to the catheter guide wire. Here, optimal is defined as the longest semi-connected group of chains with the minimum curvature (semi-connected will be defined below). This is accomplished in three parts: tree building 632, path finding 634, and curvature minimization 636. In the tree building module 632, the proximity relationships between chains is computed by organizing the chains into a tree-like structure. This is necessary because the peak finding module usually does not yield a continuous chain of pixels which corresponds to the catheter guide wire. Therefore, chains whose endpoints are semi-connected to each other become candidates for being members of the two-dimensional model of the guide wire.

A tree is comprised of a number of nodes. A node can have one parent and a number of children. There are three types of nodes: roots, which have children but not a parent, regular nodes, which have children and a parent, and leaves, which do not have children but do have a parent. In this implementation, each node corresponds to a chain in the image. The tree building process starts by first finding the longest chain from the chain finding module. This chain will serve as the root node for two trees: one tree connected to its head pixel and another tree connected to its tail pixel.

Figure 9:
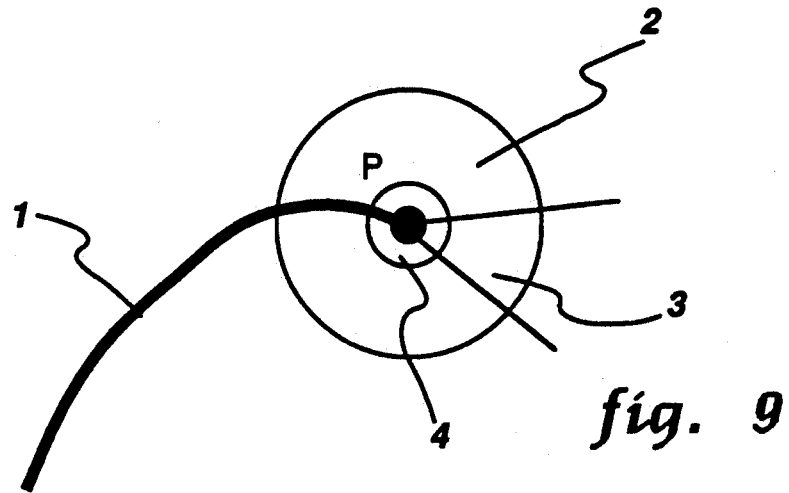
FIG. 9 is an illustration of semi-connected chains.

Building a tree is a simple recursive process which starts from a chain and works until there are no more chains that can be processed. Before the tree building process is described, the definition of "semi-connected" is supplied. FIG. 9 shows a typical scenario. The thick black line represents a chain of pixels (chain 1); the end of the chain marked by a filled black circle (pixel P) represents the pixel against which other chains are compared. Two larger circles surround this endpoint. The smaller circle forms the boundary of the principle search region. If any other chain endpoint lies in this region, it is semi-connected to chain 1. The larger circle represents the secondary search region. If the endpoint of any other chain lies in this region (but not in the principle search region) it is semi-connected to chain 1 only if it also lies in the region bounded by the two rays emanating from P. The rays are chosen such that the bisecting ray between the two rays is parallel to the direction of the end of chain 1. In this implementation the radius of the principle search region is five pixel units, the radius of the secondary search region is three times the radius of the principle search region, and the angle between the rays is one radian. Only if a chain's endpoint lies in either of these two regions is it a candidate for becoming a child of chain 1. Thus, while chains 3 and 4 might become children of chain 1, chain 2 cannot.

Figure 10A:
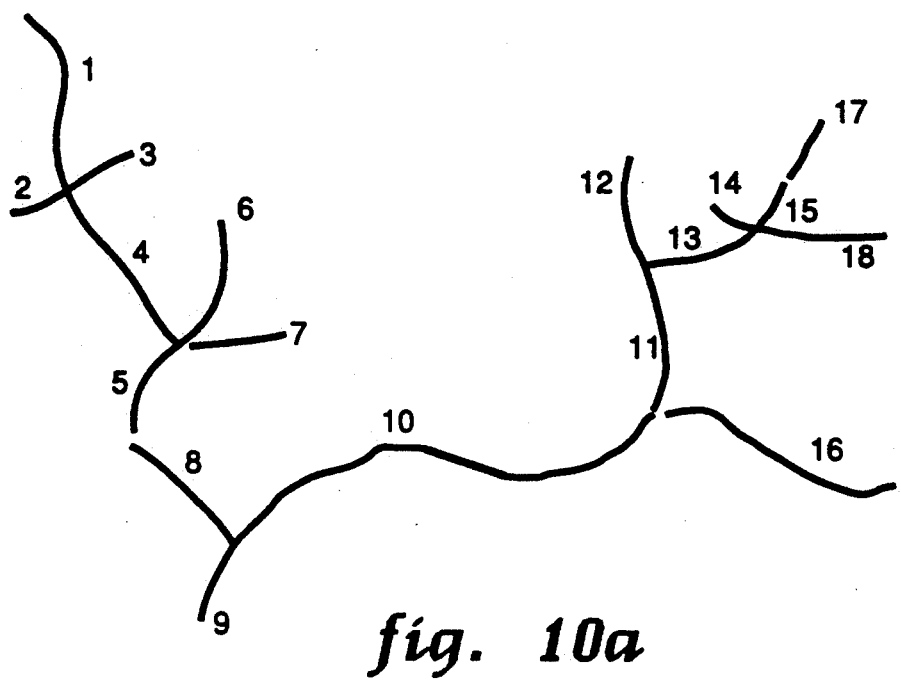
FIGS. 10a–10c illustrate tree building on a test image.
Figure 10B:
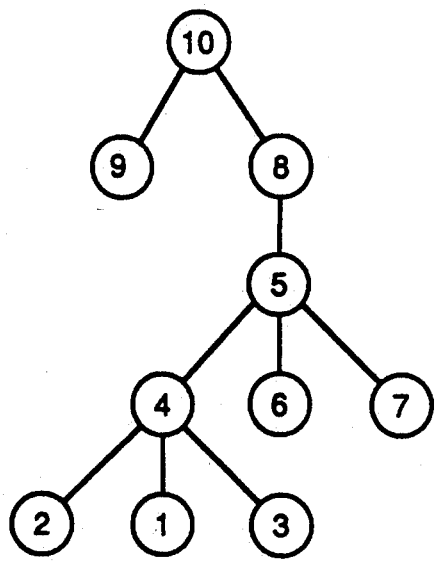
Figure 10C:
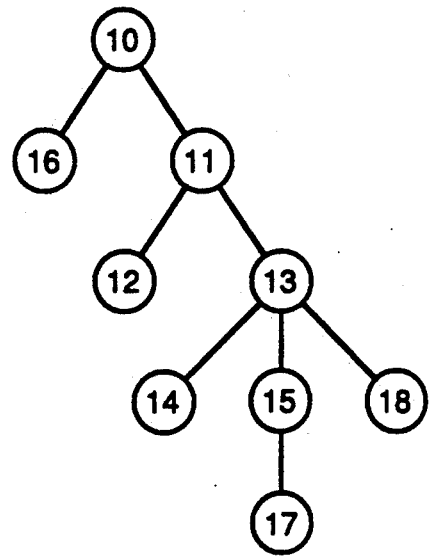

A few examples of tree building will explain the process. Examples of the tree building process on a test image is shown in FIG. 10. The chains are shown in FIG. 10a and the two resulting trees, one for the head pixel of the longest chain and one for the tail pixel, are shown in FIGS. 10b and 10c respectively. For simplicity, all chains which are relatively close to each other are considered to be semiconnected. In these trees, child nodes are shown in the tree below their parent node and the numbers inside the nodes of the trees designate the chain to which the node corresponds. Chain 10 is the longest chain in the image so both root nodes correspond to chain 10.

Figure 11:
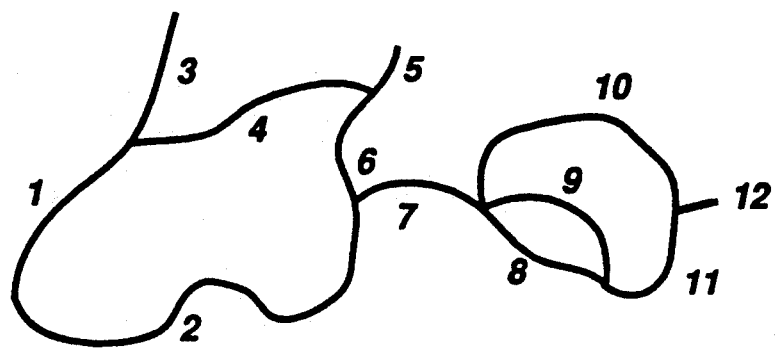
FIG. 11 illustrates a complex test image.
Figure 12A:
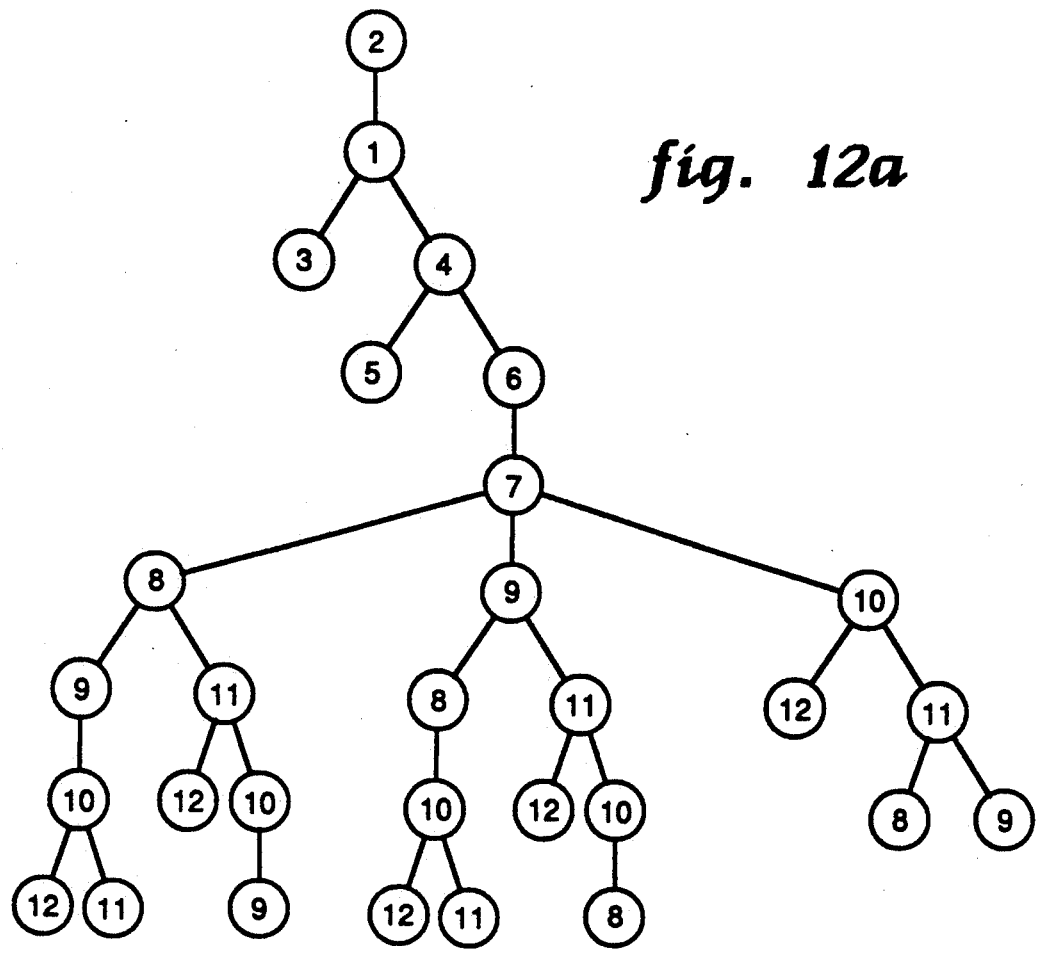
FIG. 12a–12b illustrates tree building on a complex test image.
Figure 12B:
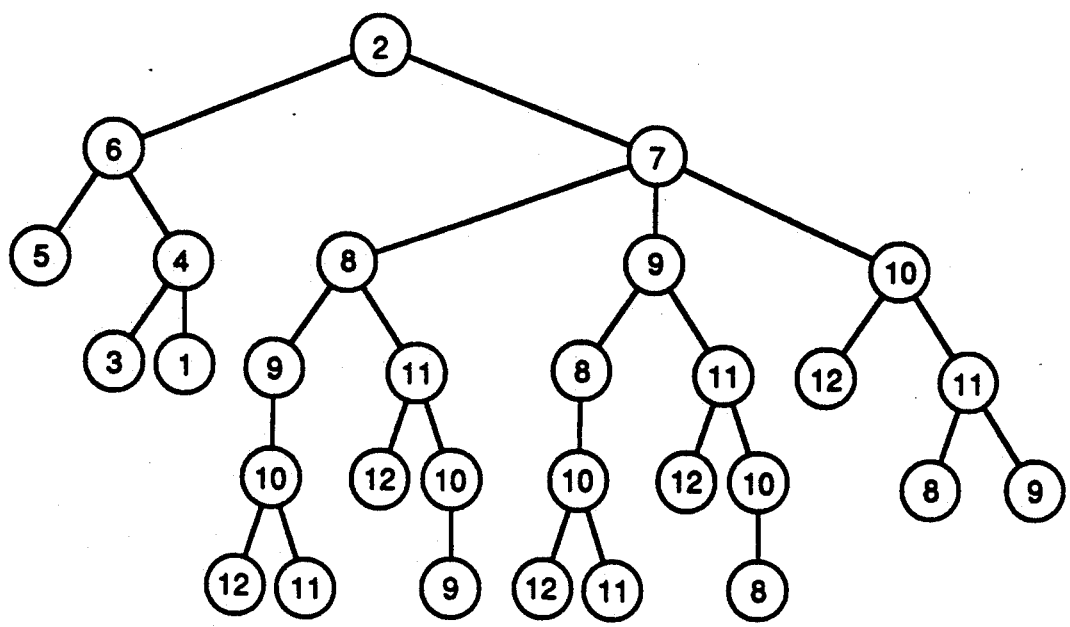

In the next example, a more complex tree building example is shown. FIG. 11 shows an image with fewer chains (12 compared with 17 in FIG. 10a) but much more complex trees (shown in FIGS. 12a-12b). The reason for this increased complexity is that the two trees formed from the endpoints of the longest chain (chain 2) are not disjoint sets; many chains appear in both trees. Also, some of the chains form loops which further complicate the process. This figure shows that there is one more constraint on the possible children of a chain in addition to being semi-connected. If chain B is semi-connected to chain A but chain B is an ancestor of chain A (parent, grandparent, etc.) then chain B cannot be a child of chain A. This prevents infinitely deep trees from forming. In the figure, once chain 9 has been designated as a child of chain 8, chains 8 or 7 cannot be children of 9 even though they are semi-connected to chain 9.

After both trees have been constructed, the longest, valid path through the nodes of the trees is discovered. This is accomplished by performing a depth first search on both trees (head tree and tail tree) and testing the path between every leaf node in one tree to every leaf node in the other tree for length and validity. A path is invalid if a chain appears twice in the path (of course, the root chain can appear in both trees). In FIG. 10a, computing the paths is relatively simple. The upper portion of FIG. 13 shows some of the 30 paths generated by these trees in the order that they are generated; the letter at the beginning of the path indicates whether the path is valid (V) or invalid (I). The lower portion of FIG. 13 shows some of the 182 paths generated for the complex example in FIG. 11. The length of the valid paths are computed by summing together the lengths of their component chains. This longest path (or paths) is then checked by the curvature minimization module.

Figure 14:
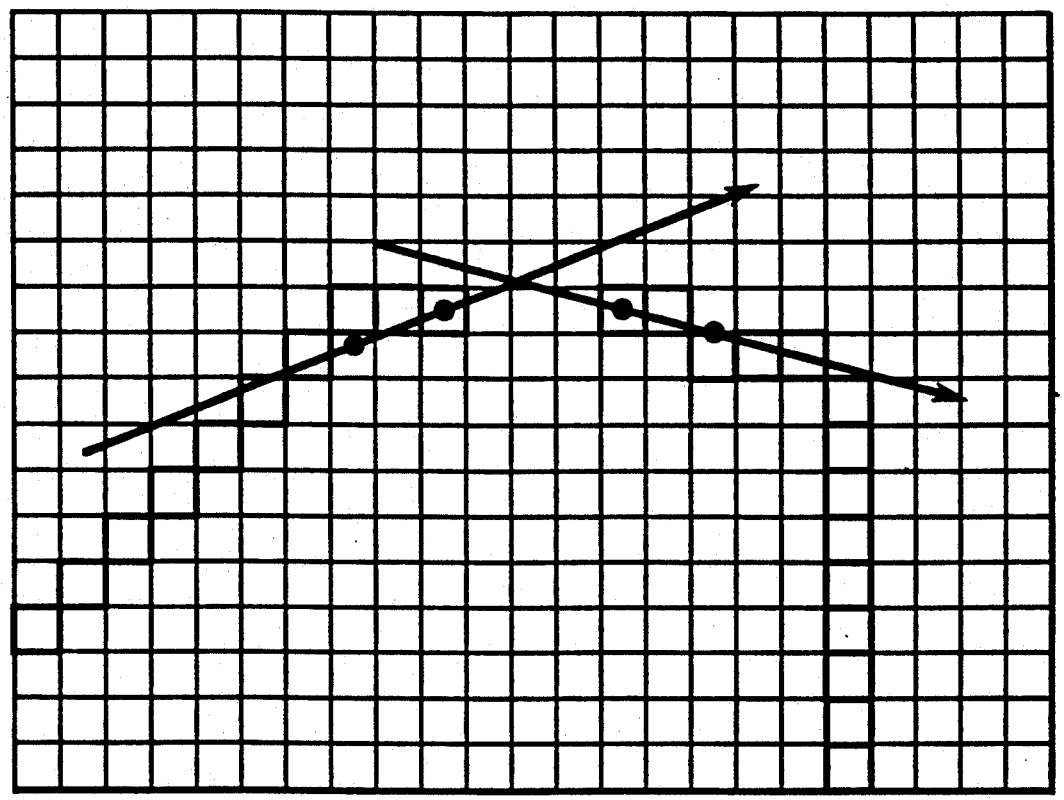
FIG. 14 illustrates angle calculation between two pixel chains.

Referring again to FIG. 6, in the curvature minimization module 836, the curvature of all the longest paths is computed to determine which is the optimal path. The curvature of a path is the sum of the difference in angle between adjacent chains in the path. FIG. 14 shows how the angle between two chains is computed. The direction of an endpoint of a chain (shown as large arrows in the figure) is computed by calculating the average position of the N pixels closest to the endpoint of the chain (N=5). Then, the x and y values of the endpoint are subtracted from this average value to obtain a direction vector. The angle between the direction vector of one chain and the direction vector of the next chain defines the angle between two chains. Of the longest paths, the path with the lowest total curvature is designated the optimal path. This path is used by the path breaking module to compute the two-dimensional model of the guide wire.

As shown by loop 630 in FIG. 6, the method now scans all the chains to find the next longest chain and starts the tree building process again. The best path is stored in a global location so that when the new optimal path (derived from using the next longest chain as the root node for the head tree and tail tree) is computed it can be compared against the old optimal path. If the new optimal path is longer than the old optimal path then the new optimal path becomes the global optimal path. This process iterates until all chains are used as roots, or a predefined limit is reached.

Figure 15:
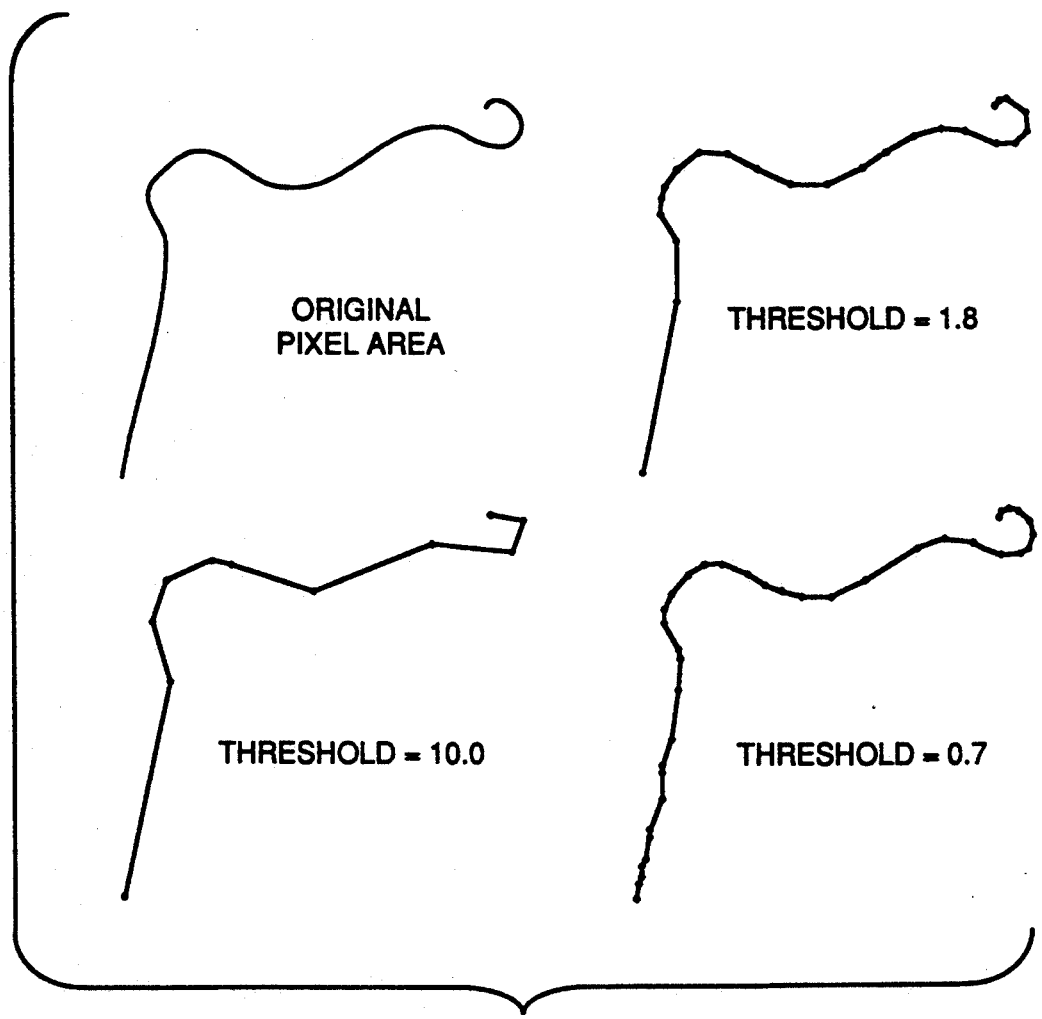
FIG. 15 illustrates the effect of varying thresholds on two-dimensional model complexity.

Finally, after the optimal path of chains has been found, the path is converted into a two-dimensional model at block 640. The two-dimensional model of the chains of pixels in the optimal path is a compact representation of the whole path; the model conveys the essence of the path without enumerating every pixel in the path. The representation of the two-dimensional model used in the present invention, is a simple, ordered, set of pixels which, when connected by lines, approximates the original path. Before any further processing, the pixels in the chains of the optimal path are dumped (in order) into an linear array of pixels. The array of pixels are recursively split into smaller and smaller segments until a certain threshold is reached; this threshold specifies the maximum distance (in pixel units) between the array of pixels and the two-dimensional model. If the distance between the line segment of the two-dimensional model and the array of pixels exceeds the threshold, the segment is split into two segments and the process is then invoked on the smaller segments. FIG. 15 shows the effect of different thresholds on the two-dimensional model created from the array of pixels. Higher thresholds will give coarse two-dimensional models but extremely small thresholds will yield two-dimensional models which too closely match the pixel grid. The dots in FIG. 15 correspond to vertices of the two-dimensional model and the lines connecting the blocks represent the ordered edges of the two-dimensional model. A threshold of three pixel units yields reasonable models.

Once the two-dimensional model is created, the temporal sequence image analyzer is able to locate the tip of the catheter and send a signal to the modulator to direct it to aim at the location on the fluoroscope detection screen corresponding to the catheter tip and the estimated offset which represents the movement of the catheter tip between frames.

The system can operate either in equispaced time mode or irregularly spaced time mode. In equispaced time mode, the X-ray dosage reduction is due to the reduction in the spatial extent of the beam and beam intensity. However, in irregularly spaced time mode, the system will incorporate time into its motion prediction model as a variable and will balance the desire to hold off acquiring an image as long as possible against the desire to not lose track of the catheter tip. If, however, the system loses track of the target of interest, it can switch to full field of view mode to reacquire the target image.

While the present invention has been described with respect to specific embodiments, many modifications, variations, alterations, substitutions, and equivalents will be apparent to those skilled in the art. Accordingly, the invention is to be considered as limited only by the spirit and scope of the appended claims.

What is claimed is:

1. A method for reducing the X-ray dosage during a fluoroscopic examination utilizing a fluoroscope with an image digitizer with storage capability and a detection screen comprising the steps of:
   exposing on the detection screen of said fluoroscope an area with an approximate shape and location of the image of a catheter tip within a patient undergoing an interventional radiological procedure;
   storing a time-sequence of digitized fluoroscopic images obtained by said exposing step wherein at least one of said images is a full field of view image; and
   combining said stored images into an output image.

2. The method of claim 1 wherein said exposing step is done in an equispaced time mode.

3. The method of claim 1 wherein said exposing step is done in an irregularly spaced time mode.

4. The method of claim 1 wherein said combining step comprises the step of:
   applying a filter function to each of said stored images, said filter function being determined for each said stored image and defining for each pixel in each said stored image a value representing a weight given to said pixel in said output image.

5. The method of claim 1 wherein said exposing step comprises the step of:
   extracting a first set of pixels defining the path of a catheter for the most recent of said stored images;
   estimating a second set of pixels which will contain the image of the tip of said catheter at the time a subsequent image is obtained; and
   modulating an X-ray beam to expose the area on said detection screen corresponding to said second set of pixels.

6. The method of claim 5 wherein said extracting step comprises the steps of:
   creating a binary peak image; and
   constructing a two-dimensional model of said catheter path from said binary peak image.

7. The method of claim 6 wherein said constructing step comprises the steps of:
   a) thinning said binary peak image;
   b) ordering said thinned binary peak image into pixel chains;
   c) organizing said pixel chains into first and second trees of pixel chains, wherein said first and second trees represent a first and second direction relative to a longest of said pixel chains and said first and second trees represent paths of semi-connected pixel chains;
   d) searching said trees for longest valid paths through the nodes of said trees;
   e) selecting the path with minimum curvature if no single valid path is longest;
   f) repeating steps c-e using a next longest of said pixel chains in step c;
   g) selecting a longest of the valid paths found in step d; and
   h) representing said longest valid path as a set of line segments.

8. An apparatus for reducing the X-ray dosage during a fluoroscopic examination utilizing a fluoroscope with an image digitizer with storage capability and a detection screen, said apparatus comprising:
   means for exposing an area on the detection screen of said fluoroscope with an approximate shape and location of the image of a catheter tip within a patient undergoing an Interventional Radiological procedure;
   means for storing a time-sequence of digitized fluoroscopic images obtained by said exposing step wherein at least one of said images is a full field of view image; and
   means for combining said stored images into an output image after each image in said time sequence of images is obtained.

9. The apparatus of claim 8 wherein said combining means comprises:
   means for applying a filter function to each of said stored images, said filter function being determined for each said stored image and defining for each pixel in each said stored image a value representing a weight given to said pixel in said output image.

10. The apparatus of claim 8 wherein said exposing means comprises:
    means for extracting a first set of pixels defining the path of a catheter, for the most recent of said stored images;
    means for estimating a second set of pixels which will contain the image of the tip of said catheter at the time a subsequent image is obtained; and
    means for modulating an X-ray beam to expose the area on said detection screen corresponding to said second set of pixels.

11. The apparatus of claim 10 wherein said extracting means comprises:
    means for creating a binary peak image; and
    means for constructing a two-dimensional model of said catheter path from said binary peak image.

12. The apparatus of claim 11 wherein said constructing means comprises:
    a) means for thinning said binary peak image;
    b) means for ordering said thinned binary peak image into pixel chains;
    c) means for organizing said pixel chains into first and second trees of pixel chains, wherein said first and second tree represent a first and second direction relative to a longest of said pixel chains and said first and second trees represent paths of semi-connected pixel chains;

d) means for searching said trees for longest valid paths through the nodes of said trees;

e) means for selecting the path with minimum curvature if no single valid path is longest;

f) means for repeating steps c-e using a next longest of said pixel chains in step c;

g) means for selecting a longest of the valid paths found in step d; and h) means for representing said longest valid path as a set of line segments.

13. The apparatus of claim 9 wherein said means for applying a filter function to each of said stored images includes a digital computer programmed to apply a filter function to each of said stored images.

14. The apparatus of claim 10 wherein said extracting means comprises a digital computer programmed to extract a first set of pixels defining the path of a catheter, for the latest of said stored images and said estimating means includes a digital computer programmed to estimate a second set of pixels which will contain the image of said catheter's tip at the time the next image is obtained.

15. The apparatus of claim 14 wherein said digital computer programmed to extract a first set of pixels defining the path of a catheter, for the latest of said stored images is programmed to:

create a binary peak image; and construct a two-dimensional model of said catheter path.

16. The apparatus of claim 15 wherein said compute programmed to construct a two-dimensional model of said catheter path is programmed to:

a) thin said binary peak image;

b) order said thinned binary peak image into pixel chains;

c) organize said pixel chains into first and second trees of pixel chains, wherein said first and second tree represent a first and second direction relative to the longest of said pixel chains and said first and second trees represent paths of semi-connected pixel chains;

d) search said trees for longest valid paths through the nodes of said trees;

e) select the path with minimum curvature if no single valid path is longest;

f) repeat steps c-e using a next longest of said pixel chains in step c;

g) select a longest of the valid paths found in step d; and h) represent said longest valid path as a set of line segments.

* * * * *